US00PP33567P2

(12) United States Plant Patent
Whitehead

(10) Patent No.: US PP33,567 P2
(45) Date of Patent: Oct. 19, 2021

(54) ***ILEX* TREE NAMED 'IPOC'**

(50) Latin Name: *Ilex opaca*
Varietal Denomination: IPOC

(71) Applicant: HortSource LLC, Lincolnton, GA (US)

(72) Inventor: Dan Milton Whitehead, Lincolnton, GA (US)

(73) Assignee: HORTSOURCE LLC, Lincolnton, GA (US)

( * ) Notice: Subject to any disclaimer, the term of this patent is extended or adjusted under 35 U.S.C. 154(b) by 0 days.

(21) Appl. No.: 17/099,218

(22) Filed: Nov. 16, 2020

(51) Int. Cl.
*A01H 5/00* (2018.01)

(52) U.S. Cl.
USPC ..... Plt./247

(58) Field of Classification Search
USPC ..... Plt./247
See application file for complete search history.

*Primary Examiner* — Annette H Para
(74) *Attorney, Agent, or Firm* — Penny J. Aguirre

(57) ABSTRACT

A new cultivar of *Ilex opaca* tree named 'IPOC' that is characterized by its upright narrow plant habit when mature; reaching about 17 m in height and 6.7 m in width, its foliage that is slightly large in size, its foliage that is dark green in color, and its heavy berry set.

2 Drawing Sheets

Botanical classification: *Ilex opaca.*
Variety denomination: 'IPOC'.

BACKGROUND OF THE INVENTION

The present invention relates to a new and distinct cultivar of *Ilex opaca* and will be referred to hereafter by its cultivar name, 'IPOC'. 'IPOC' is a new cultivar of American holly grown for use as an ornamental landscape plant.

'IPOC' was discovered by the Inventor as a chance seedling that was growing in a boulevard garden in Clinton, S.C. in October 2019. The parentage is unknown, however based on its characteristics it is believed to be derived as a seedling of *Ilex opaca.*

Asexual propagation of the new cultivar was first accomplished by the Inventor using semi-hardwood stem cuttings in July of 2020 in Rutledge, Ga. Asexual propagation by semi-hardwood stem cuttings has determined that the characteristics of the new cultivar are stable and are reproduced true to type in successive generations.

SUMMARY OF THE INVENTION

The following traits have been observed repeatedly and represent the characteristics of the new cultivar. These attributes in combination distinguish 'IPOC' as a unique cultivar of *Ilex.*

1. 'IPOC' exhibits an upright narrow plant habit when mature; reaching about 17 m in height and 6.7 m in width.
2. 'IPOC' exhibits foliage that is slightly large in size.
3. 'IPOC' exhibits foliage that is dark green in color.
4. 'IPOC' exhibits a heavy berry set.

'IPOC' can be most closely compared to the *Ilex opaca* cultivars 'Satyr Hill' (not patented) and 'Dan Fenton' (not patented). 'Satyr Hill' is similar to 'IPOC' in being a female plant with berry set. 'Satyr Hill' differs from 'IPOC' in having a less narrow plant habit, foliage that is smaller in size and lighter green in color. 'Dan Fenton' is similar to 'IPOC' is similar to 'IPOC' in in being a female plant with berry set and having foliage that is dark green in color. 'Dan Fenton' differs from 'IPOC' in having a less narrow plant habit, foliage that is slightly smaller in size, and foliage that is more open (less dense).

BRIEF DESCRIPTION OF THE DRAWINGS

The accompanying colored photographs illustrate the overall appearance and distinct characteristics of a mature tree of the new cultivar as grown outdoors in Clinton, S.C. The age of the tree is unknown, however it is estimated to be 80 years in age.

The photograph in FIG. 1 provides a side view of the plant habit of 'IPOC'.

Figure 1:
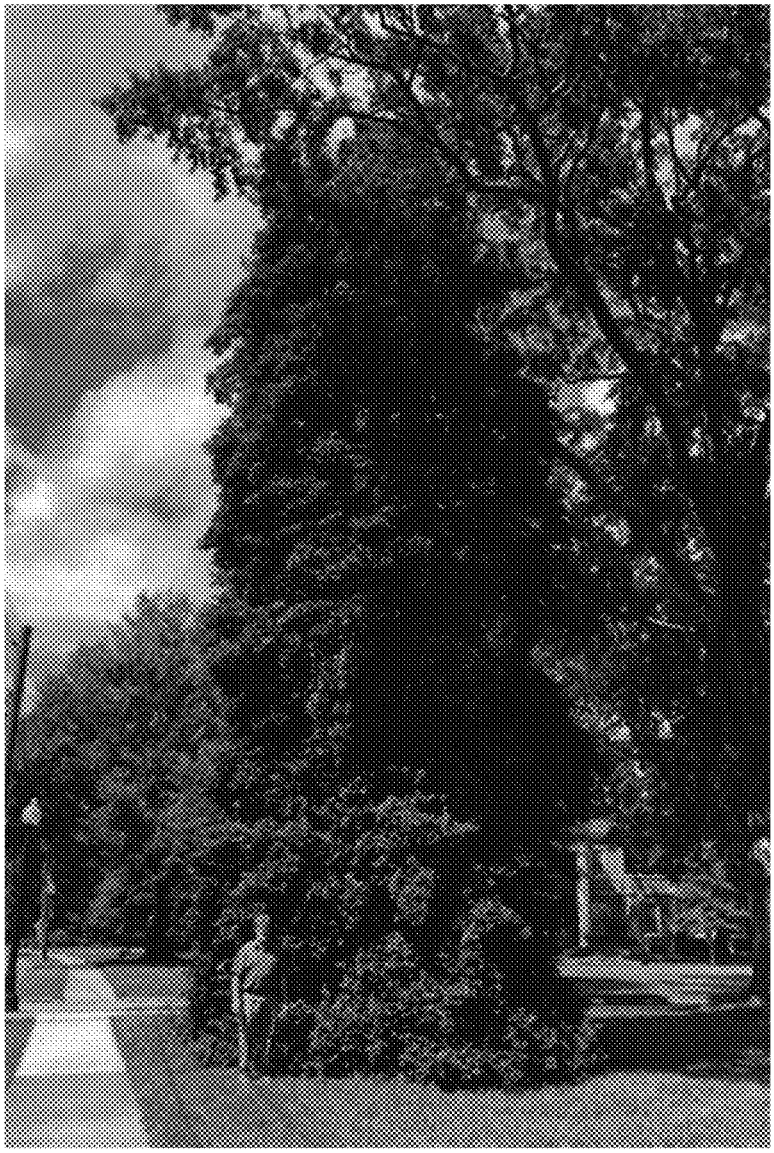
Figure 2:
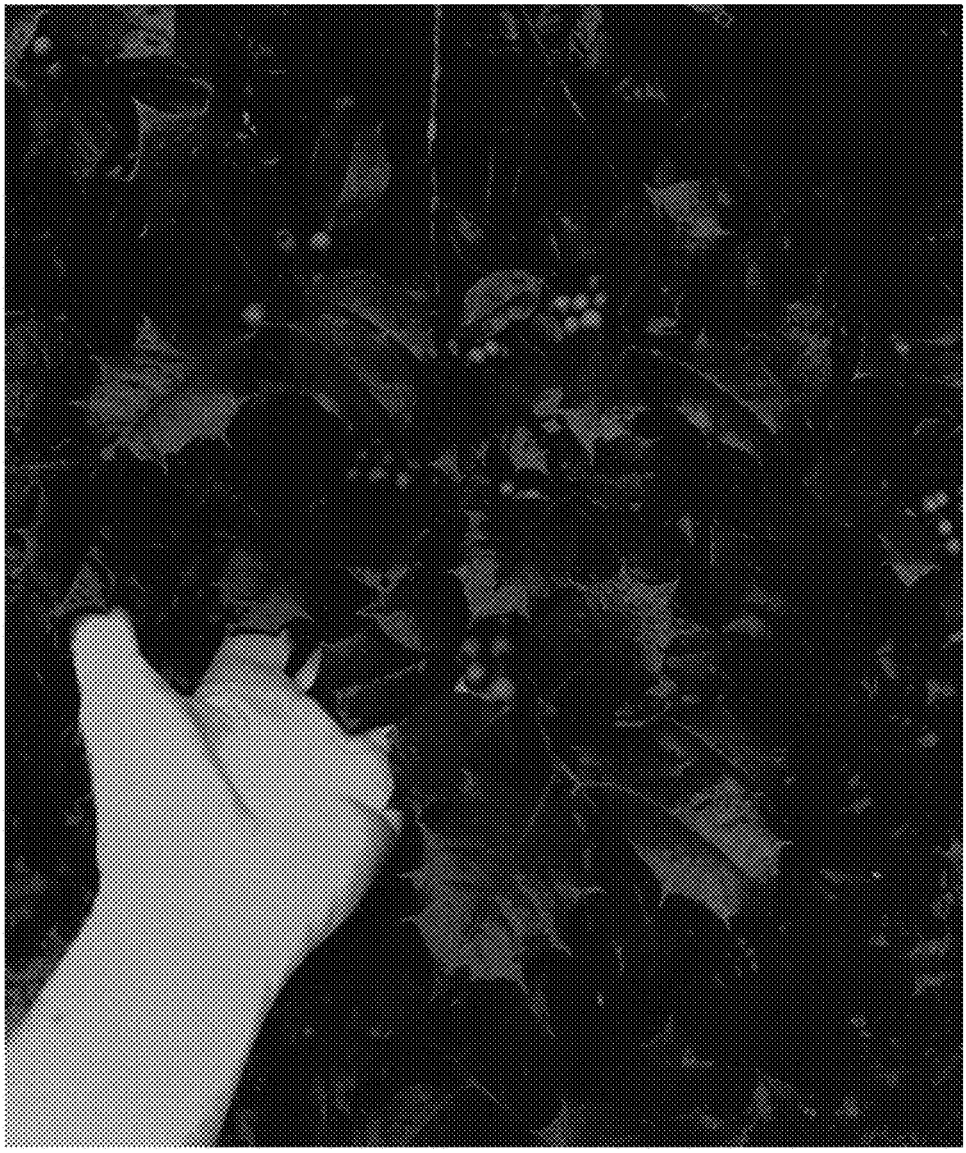

The photograph in FIG. 2 provides a close-up view of foliage and berries of 'IPOC'.

The colors in the photographs may differ slightly from the color values cited in the detailed botanical description, which accurately describe the colors of the new *Ilex.*

DETAILED BOTANICAL DESCRIPTION

The following is a detailed description of three-year-old plants of the new cultivar grown outdoors in 1-quart containers in Rutledge, Ga. with other data collected from the original discovered plant about 80 years in age. The phenotype of the new cultivar may vary with variations in environmental, climatic, and cultural conditions, as it has not been tested under all possible environmental conditions. The color determination is in accordance with The 2001 Colour Chart of The Royal Horticultural Society, London, England, except where general color terms of ordinary dictionary significance are used.

General description:

*Blooming period.*—March to May in Georgia.
*Plant type.*—Evergreen, perennial tree.
*Plant habit.*—Upright and narrow pyrimidal.
*Height and spread.*—Reaches an average of 17 m in height and 6.7 m in spread when mature.
*Hardiness.*—At least in U.S.D.A Zones 6 to 8.

*Diseases and pests*.—No susceptibility to diseases has been observed.

*Root description*.—Densely fibrous and closest to 165C in color.

*Propagation*.—Semi-hardwood stem cuttings.

*Root development*.—Cuttings root in 25 days during summer in a plug, root development from time of softwood cuttings to a finished rooted quart container is 5 to 7 weeks.

*Growth rate*.—Moderate.

Branch description:

*Branching*.—Freely branching; 5 main branches each with numerous lateral branches per main branch.

*Stem size*.—Main branches; an average of 1 m in height and 5 cm in width 10 cm above soil line, lateral branches; an average of 1 m in length and 3 mm in diameter.

*Branch surface*.—Glabrous and matte.

*Branch shape*.—Pentagonal.

*Branch aspect*.—Slightly ascending to nearly horizontal at the base, emerging at 80° to 90° from the trunk, upper branches are more ascending emerging at 30° or more from the trunk.

*Branch strength*.—Very strong.

*Branch color*.—Young branches; 199B, mature branches; 197C.

*Internode length*.—Average of 2 cm.

Foliage description:

*Leaf shape*.—Elliptic to elliptic-lanceolate.

*Leaf division*.—Simple.

*Leaf base*.—Rounded.

*Leaf apex*.—Acute.

*Leaf fragrance*.—None.

*Leaf venation*.—Banchidrome, pinnate, upper surface veins 147B, lower surface veins 145A.

*Leaf margins*.—Pectinate, entire, spiny.

*Leaf arrangement*.—Alternate.

*Leaf aspect*.—Moderately to strongly undulate.

*Leaf attachment*.—Petiolate.

*Leaf surface*.—Upper surface smooth and glabrous. lower surface smooth to minutely downy.

*Leaf size*.—Average of 6.7 cm in length, 5.2 cm in width.

*Leaf quantity*.—Average of 65 per lateral branch.

*Leaf color*.—Mature leaves upper surface; 147A, mature leaves lower surface; 137D to 138B.

*Petioles*.—Average of 1 cm in length, smooth and glabrous surface surface, 147B in color.

Flower description:

*Inflorescence type*.—Cluster of female flowers at axile of lateral branches.

*Inflorescence*.—Clustered axillary cyme, an average of 1.3 cm in height, 1.1 cm in diameter.

*Lastingness of flowers*.—Average of 7 days persistent, self-cleaning.

*Flower size*.—An average of 10 mm in height and width.

*Flower fragrance*.—None.

*Flower number*.—An average of 12 flowers per cluster, 200 flowers per plant.

*Flower aspect*.—Upright to outward, cupped.

*Flower type*.—Rotate, single.

*Flower buds*.—Globular in shape, smooth, glabrous and matte surface, an average of 3 mm in length and 2 mm in width, color; 54C.

*Petals*.—4 to occasionally 5, broad oblong, slightly concave in shape, base fused, glabrous, slightly velvety and very slightly glossy, entire margins, 2 mm in length, 1.7 mm in diameter, when opening and fully open upper and lower surface 155B, slightly tinged at the top 91B.

*Calyx*.—Rotate, cup-shaped, 1.5 mm in length, 2 mm in diameter.

*Sepal*.—Rotate, 4 to occasionally 5, an average of 1.3 mm in length and 1.1 mm in width, broad ovate in shape, entire margin, broad cuneate base, upper and lower surface smooth, glabrous, matte, color; both surfaces 144B.

*Peduncle*.—Round in shape, an average of 1 mm in length, 1 mm in diameter, held in an average angle of 30° , strong, smooth and glabrous surface, 175A in color.

*Pedicel*.—Round in shape, an average of 1 mm in length, 1 mm in diameter, held in an average angle of 90° , moderately strong, smooth and glabrous surface, 155A in color.

Reproductive organs:

*Gynoecium*.—1, pistil: About 3 mm in length, style: about 3 mm on length, and 144C in color, Stigma: globular in shape, stigma: color: about 151A on color, ovary: 151B on color.

*Androecium*.—None, female flowers only.

*Fruit/seeds*.—Berry like drupe, round in shape, an average of 8 mm in height and diameter, satiny surface, immature color N144C maturing to 179A in color, seeds; 4, an average of 6 mm in length and 2 mm in width, oblong in shape with a flattened side, 160B in color, an average of 7 to 9 berries per flowering leaf axil.

It is claimed:

1. A new and distinct cultivar of *Ilex* tree named 'IPOC' as herein illustrated and described.

* * * * *